United States Patent
Chen et al.

(10) Patent No.: US 10,482,745 B2
(45) Date of Patent: Nov. 19, 2019

(54) HEAD LOWERING AND TURNING REMINDING DEVICE, CONTROL METHOD THEREOF AND HELMET

(71) Applicant: BOE Technology Group Co., Ltd., Beijing (CN)

(72) Inventors: Shuo Chen, Beijing (CN); Xinxin Mu, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 5 days.

(21) Appl. No.: 15/542,252

(22) PCT Filed: Jun. 17, 2016

(86) PCT No.: PCT/CN2016/086209
§ 371 (c)(1),
(2) Date: Jul. 7, 2017

(87) PCT Pub. No.: WO2017/143702
PCT Pub. Date: Aug. 31, 2017

(65) Prior Publication Data
US 2018/0108238 A1    Apr. 19, 2018

(30) Foreign Application Priority Data

Feb. 25, 2016 (CN) .......................... 2016 1 0105874

(51) Int. Cl.
*B60Q 1/00* (2006.01)
*G08B 21/04* (2006.01)
(Continued)

(52) U.S. Cl.
CPC .......... *G08B 21/0446* (2013.01); *A42B 3/046* (2013.01); *A42B 3/0433* (2013.01);
(Continued)

(58) Field of Classification Search
CPC .. G08B 21/0046; G08B 21/24; G08B 21/182; G08G 1/052; A42B 3/0453; A42B 3/046;
(Continued)

(56) References Cited

U.S. PATENT DOCUMENTS 7,480,570 B2 *  1/2009 Yopp ..................... B60W 30/16
                                                    340/435
9,579,060 B1 *  2/2017 Lisy ..................... A61B 5/6803
(Continued)

FOREIGN PATENT DOCUMENTS

CN       201210338 Y       3/2009
CN       101667323 A       3/2010
(Continued)

OTHER PUBLICATIONS

May 31, 2017—(CN) Office Action Application 201610105874.2 with English Translation.
(Continued)

*Primary Examiner* — Anh V La
(74) *Attorney, Agent, or Firm* — Banner & Witcoff, Ltd.

(57) ABSTRACT

A head lowering and turning reminding device, a control method thereof and a helmet are disclosed. The reminding device is disposed on a vehicle or worn by a user of the vehicle, and includes: a speed sensor configured to detect a ground speed of the vehicle; a head posture monitoring module configured to monitor a head posture of the user and generate a signal relevant to a head rotating action of the user; a recognition module configured to receive the signal and recognize at least one of a head lowering action and a head turning action of the user and a duration time of this action; and an alarm module configured to output an alarm for reminding the user upon the ground speed being greater than a speed threshold and the duration time exceeding a preset time threshold.

17 Claims, 3 Drawing Sheets

(51) Int. Cl.
*A61B 5/11* (2006.01)
*A42B 3/04* (2006.01)
*G08B 21/18* (2006.01)
*G08B 21/24* (2006.01)
*G08G 1/052* (2006.01)
*A61B 5/00* (2006.01)

(52) U.S. Cl.
CPC .............. *A42B 3/0453* (2013.01); *A61B 5/11* (2013.01); *G08B 21/182* (2013.01); *G08B 21/24* (2013.01); *G08G 1/052* (2013.01); *A61B 5/1116* (2013.01); *A61B 5/6803* (2013.01); *A61B 2503/10* (2013.01)

(58) Field of Classification Search
CPC ....... A42B 3/0433; A61B 5/1116; A61B 5/11; A61B 5/6803; A61B 2503/10
USPC .................................................. 340/457, 432
See application file for complete search history.

(56) References Cited

U.S. PATENT DOCUMENTS

| | | | | |
|---|---|---|---|---|
| 2008/0080741 | A1* | 4/2008 | Yokoo | B60W 40/09 |
| | | | | 382/104 |
| 2012/0069301 | A1* | 3/2012 | Hirata | A61B 3/112 |
| | | | | 351/209 |
| 2015/0061815 | A1 | 3/2015 | Yang et al. | |
| 2015/0252540 | A1 | 9/2015 | Lee | |
| 2016/0070966 | A1* | 3/2016 | Yang | G06K 9/00335 |
| | | | | 345/8 |
| 2016/0171864 | A1* | 6/2016 | Ciaramelletti | A42B 3/046 |
| | | | | 340/539.12 |
| 2016/0207455 | A1* | 7/2016 | Kim | B60K 28/066 |

FOREIGN PATENT DOCUMENTS

| | | |
|---|---|---|
| CN | 202088896 U | 12/2011 |
| CN | 202183155 U | 4/2012 |
| CN | 102436715 A | 5/2012 |
| CN | 103050028 A | 4/2013 |
| CN | 104002760 A | 8/2014 |
| CN | 203941599 U | 11/2014 |
| CN | 104401249 A | 3/2015 |
| CN | 104424751 A | 3/2015 |
| CN | 104573657 A | 4/2015 |
| CN | 105575048 A | 5/2016 |
| CN | 205375752 U | 7/2016 |
| JP | 2014123883 A | 7/2014 |
| KR | 101399582 B1 | 6/2014 |

OTHER PUBLICATIONS

Nov. 25, 2016—(WO) International Search Report and Written Opinion Application PCT/CN2016/086209 with English Translation.

Feb. 1, 2018—(CN) Second Office Action Appn 201610105874.2 with English Tran.

\* cited by examiner

HEAD LOWERING AND TURNING REMINDING DEVICE, CONTROL METHOD THEREOF AND HELMET

The application is a U.S. National Phase Entry of International Application No. PCT/CN2016/086209 filed on Jun. 17, 2016, designating the United States of America and claiming priority to Chinese Patent Application No. 201610105874.2, filed Feb. 25, 2016. The present application claims priority to and the benefit of the above-identified applications and the above-identified applications are incorporated by reference herein in their entirety.

TECHNICAL FIELD

Embodiments of the present disclosure relate to a head lowering and turning reminding device, a control method thereof, and a helmet.

BACKGROUND

Currently, cycle racing and electric bicycles become more and more popular. During riding, several safety risks may be involved when a rider lowers or turns his/her head for a long time. However, conventional bicycles usually lack relevant reminding devices.

SUMMARY

At least one embodiment of the present disclosure provide a head lowering and turning reminding device, a control method thereof and a helmet, which can detect actions of a specific object in two directions during head lowering and head turning and output an alarm when detecting a head lowering or head turning action last for a too long time, so as to avoid traffic accidents.

In order to achieve the above objectives, the embodiments of the present disclosure adopt technical solutions as below.

The embodiments of the present disclosure provide a head lowering and turning reminding device disposed on a vehicle or worn by a user of the vehicle, including: a speed sensor configured to detect a ground speed of the vehicle; a head posture monitoring module configured to monitor a head posture of the user and generate a signal relevant to a head rotating action of the user; a recognition module configured to receive the signal generated by the head posture monitoring module, and recognize at least one action of a head lowering action and a head turning action of the user and a duration time of the user holding this action according to the signal; and an alarm module configured to output an alarm for reminding the user upon the ground speed of the vehicle being greater than a speed threshold and the duration time of the user holding the head lowering action or the head turning action exceeding a preset time threshold.

In an example, the head posture monitoring module is a gyroscope.

In an example, the head posture monitoring module includes a compass.

In an example, the speed sensor is a laser velometer or a radar velometer.

In an example, the recognition module is a microcontroller.

In an example, the reminding device further includes a power module configured to supply power for the speed sensor, the head posture monitoring module, the recognition module and the alarm module.

The embodiments of the present disclosure further provide a helmet including the foregoing head lowering and turning reminding device.

The embodiments of the present disclosure further provide a control method of the foregoing head lowering and turning reminding device, including:

S1: acquiring a ground speed of the vehicle;

S2: determining whether the ground speed as acquired is greater than a preset speed threshold;

S3: if the ground speed is greater than the preset speed threshold, assigning a value 0 to an action continuation parameter and executing the step S4; or else, executing the step S1;

S4: acquiring an angular velocity of a head rotating action of the user of the vehicle and a time cost by the head rotating action;

S5: calculating an angle of the head rotating action according to the angular velocity of the head rotating action and the time cost by the head rotating action as acquired;

S6: determining whether the angle of the head rotating action is greater than a preset angle threshold; if so, executing the step S7; and if not, executing the step S4;

S7: adding 1 to the value of the action continuation parameter;

S8: determining whether the current action continuation parameter is greater than a preset continuation threshold; if so, executing the step S9; and if not, executing the step S4;

S9: acquiring the ground speed of the vehicle again and determining whether the ground speed is greater than the preset speed threshold; if so, executing the step S10; and if not, executing the step S1; and S10: outputting an alarm for reminding the user.

In an example, the head rotating action includes: a head raising action that the head moves upwards, a head lowering action that the head moves downwards, and a head turning action that the head moves leftwards and rightwards.

In an example, the preset continuation threshold is configured by: acquiring a time T0 required for executing the steps S3 to S7; and dividing a preset, action duration time by the time T0 as required, and rounding the division result to obtain the preset continuation threshold.

In an example, the control method further includes: before the step S1, initializing the speed sensor, the head posture monitoring module and the recognition module.

In an example, in the step S4, a gyroscope is adopted to acquire the angular velocity of the head rotating action and the time cost by the head rotating action.

The head lowering and turning reminding device, the control method thereof and the helmet provided by the embodiments of the present disclosure detect a ground speed of a vehicle, monitor a head posture of a user of the vehicle, recognize a head lowering or turning action and a duration time of user holding this action according to the monitoring data, and output an alarm for reminding the user when the ground speed of the vehicle is greater than a speed threshold and the duration time of user holding the head lowering or turning action exceeds a preset time threshold; in this way, an alarm is activated in case of a head lowering or turning action last for a long time, so as to avoid traffic accidents.

BRIEF DESCRIPTION OF THE DRAWINGS

Hereafter, the embodiments of the present disclosure will be described in a more detailed way with reference to the accompanying drawings, so as make one person skilled in the art be able to understand the present disclosure more clearly, wherein.

DETAILED DESCRIPTION

Hereafter, the technical solutions in the embodiments of the present disclosure will be described in a clearly and fully understandable way in connection with the drawings in the embodiments of the present disclosure. It is obvious that the described embodiments are just a part but not all of the embodiments of the disclosure. Based on the described embodiments herein, one person skilled in the art can obtain other embodiment(s), without any inventive work, which should be within the scope of the disclosure.

Unless otherwise defined, the technical terminology or scientific terminology used herein should have the same meaning as commonly understood by one of ordinary skill in the art to which this disclosure belongs. Likewise, terms like "first," "second," etc., which are used in the description and the claims of the present application for disclosure, are not intended to indicate any sequence, amount or importance, but distinguish various components. The phrases "connect", "connected", etc., are not intended to define a physical connection or mechanical connection, but may include an electrical connection, directly or indirectly. "On," "under," "left," "right" or the like is only used to describe a relative positional relationship, and when the absolute position of a described object is changed, the relative positional relationship might also be changed accordingly.

Figure 1:
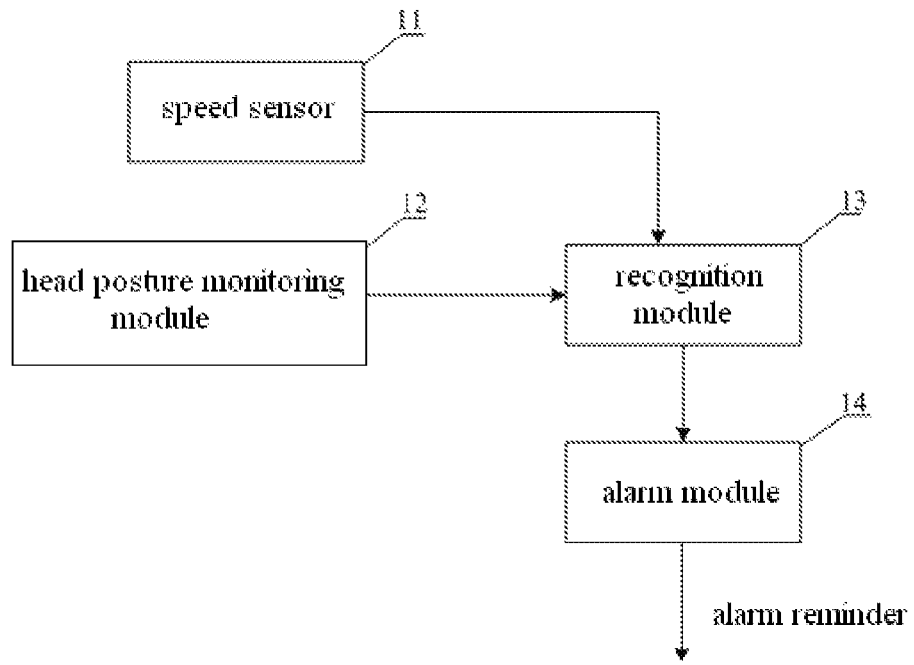
FIG. 1 is a schematic structural view of an illustrative head lowering and turning reminding device provided by an embodiment of the present disclosure.

As illustrated in FIG. 1, an embodiment of the present disclosure provides a head lowering and turning reminding device which is disposed on a vehicle or worn by a user of the vehicle. The head lowering and turning reminding device includes a speed sensor 11 configured to detect a ground speed of the vehicle; a head posture monitoring module 12 configured to monitor a head posture of the user; a recognition module 13 configured to receive a signal of the head posture monitoring module 12 and recognize a head lowering action or a head turning action of the user, as well as a duration time of the user holding the action, according to the signal; and an alarm module 14 configured to output an alarm for reminding the user when the ground speed of the vehicle is greater than a speed threshold and when the duration time of the user holding the head lowering action or head turning action exceeds a preset time.

In the embodiment, the speed sensor 11 is configured to detect the ground speed of the vehicle. The specific implementation of the speed sensor is not limited in the embodiments and may be any implementation well-known by those skilled in the art, for instance, detection via a laser velometer or a radar velometer. In the embodiment, the head posture monitoring module 12 is cooperated with the recognition module 13; the head posture monitoring module 12 is configured to monitor the head posture of the user; and the recognition module 13 performs necessary process on monitoring data obtained by the head posture monitoring module 12 and recognizes the head lowering action or the head turning action as well as the duration time of the user holding the action. The two modules may also be implemented by various ways. The specific implementation of the two modules is not limited in the embodiment and may be any implementation well-known by those skilled in the art. For instance, the head posture monitoring module 12 may be a camera configured to obtain an image of the user's head. The recognition module 13 may determine whether the user makes a head lowering or turning action during a monitoring time period by image processing method; if so, it obtains the duration time of the user holding the action by image comparison method.

In addition, the head posture monitoring module 12 may also be a gyroscope or a compass. The gyroscope is a device for measuring a angular velocity data by detecting an angular motion of a momentum moment-sensitive housing of a high-speed rotary body about one or two axes in orthogonal intersection with a rotating axis thereof, with respect to an inertial space (other angular motion detection devices that have the same function and work based on other principles may also be referred to as a gyroscope). The gyroscope may monitor an angular velocity in one or two directions and may also output a change in acceleration during a single motion (e.g., turning head for one time), through which both of the single motion and the duration time of the user holding this motion may be recognized. The gyroscope is widely applied in mobile phones, navigation devices, game sensors, etc. The gyroscope and related data processing technology have been matured and can be easily applied in the technical solutions of the embodiments provided by the present application. The compass may, in combination with data processing technology, detect a motion in a non-vertical plane and can also recognize the head lowering action and the head turning action.

The recognition module 13 in the present embodiment is configured to perform data process and logic judgment, and may be implemented by a logic unit such as a microcontroller. The recognition module 13 may also be configured to determine whether the ground speed of the vehicle is greater than a speed threshold and whether the duration time of the user holding the head lowering action or head turning action exceeds a preset time; and may output a control signal to the alarm module 14 if an alarm condition is satisfied. The alarm module 14 outputs an alarm for reminding the user upon receiving the control signal, by ways of, for example but not limited to, human voice, whistle, light flashing, etc.

Optionally, in some examples, the alarm module 14 may also be configured to determine whether the ground speed of the vehicle is greater than the speed threshold and whether the duration time of the user holding the head lowering action or head turning action exceeds the preset time. In these examples, the alarm module may include: a first determination sub-module configured to determine whether the ground speed of the vehicle is greater than the speed threshold; a second determination sub-module configured to determine whether the duration time of the user holding the head lowering action or head turning action exceeds the preset time; and a prompt sub-module configured to output an alarm for reminding the user when the ground speed of the vehicle is greater than the speed threshold and the duration time of the user holding the head lowering action or head turning action exceeds the preset time. As for utilizing which module to realize the determination function, it may be designed by those skilled in the art according to actual conditions in practice. No specific limitation will be given in the embodiment.

The head lowering and turning reminding device provided by the embodiment of the present disclosure outputs an alarm to remind the user of a danger condition when the ground speed of the vehicle is greater than the speed threshold and the duration time of the user holding the head lowering action or head turning action exceeds the preset time, so as to avoid the occurrence of traffic accidents.

In some examples, the reminding device may further include: a power module configured to supply power for the speed sensor 11, the head posture monitoring module 12, the recognition module 13 and the alarm module 14. When the reminding device is provided with the power module, it may be separated from a charger after being charged and hence can be conveniently carried for use.

Figure 2:
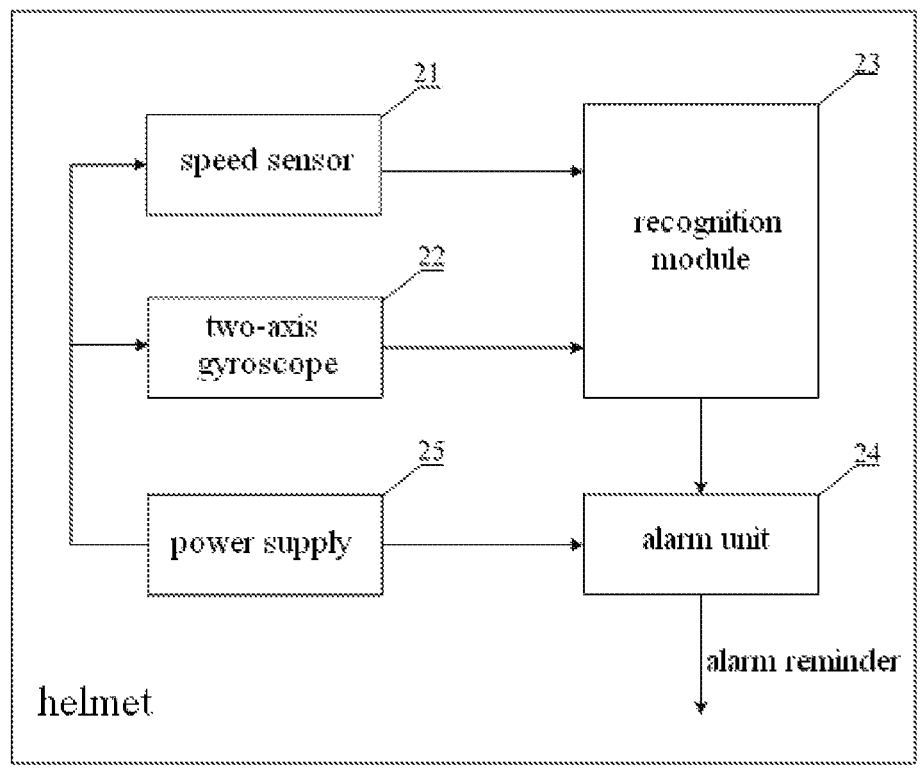
FIG. 2 is a schematic structural view of an illustrative cycling helmet with safety alarm function provided by an embodiment of the present disclosure.

As illustrated in FIG. 2, the embodiment of the present disclosure further provides a racing helmet with safety alarm function. The head lowering and turning reminding device provided by any of the foregoing embodiments may be disposed on the racing helmet.

In the embodiment of the present disclosure, the riding helmet includes: a helmet body; and a posture measuring portion, a speed sensing portion, a recognition portion and an alarm portion which are disposed on the helmet body.

Figure 3:
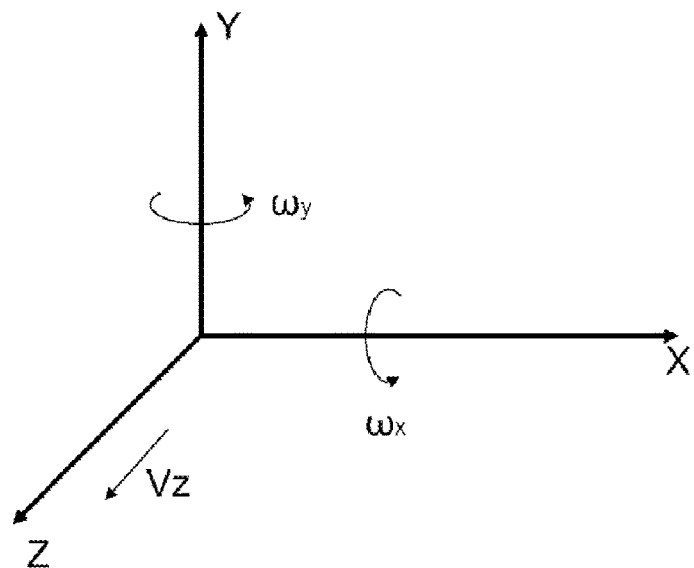
FIG. 3 is a schematic diagram illustrating a coordinate space of a two-axis gyroscope in the illustrative head lowering and turning reminding device provided by the embodiment of the present disclosure.

As illustrated in FIG. 2, the posture measuring portion includes a two-axis gyroscope 22 (corresponding to the head posture monitoring module 12 in the head lowering and turning reminding device). As illustrated in FIG. 3, the two-axis gyroscope 22 may measure angular velocity information wx and wy of a rotation action along X-axis direction and Y-axis direction, respectively; in which wx represents the angular velocity of the up-and-down rotation of the head (namely the X-axis direction) and wy represents the angular velocity of the left-and-right rotation of the head (namely the Y-axis direction). The two-axis gyroscope may adopt a micro electromechanical system (MEMS) gyroscope chip which has small volume and low cost; for instance, ADXRS290 commercially available from ADI Company.

As illustrated in FIG. 2, the speed sensing portion includes a speed sensor 21 (corresponding to the speed sensor 11 in the head lowering and turning reminding device). The speed sensor 21 may measure a velocity value along Z axis, which is the movement direction of a bicycle; namely the speed sensor 21 may measure the movement velocity of the bicycle.

As illustrated in FIG. 2, the recognition portion includes a recognition module 23 (corresponding to the recognition module 13 in the head lowering and turning reminding device). The recognition module 23 receives a data from the speed sensor 21 and the two-axis gyroscope 22, processes the data, detects an angular variation of the user's head and a duration time of the user holding an angular deflection, and outputs a control signal for alarm when recognizing a safety risk caused by the head lowering or turning action which is last for a too long time.

As illustrated in FIG. 2, the alarm portion includes an alarm unit 24 (corresponding to the alarm module 14 in the head lowering and turning reminding device). The alarm unit 24 utilizes a micro motor to generate a vibration signal to prompt the wearer after acquiring the control signal for alarm.

The above-mentioned posture measuring portion, speed sensing portion, recognition portion and alarm portion, for instance, may be embedded into the helmet body; and may be embedded, along with, for example, a power supply 25 (e.g., batteries), into the helmet body to supply the system with electric power.

Description will be given below to the illustrative working process of the helmet provided by the embodiment of the present disclosure for more clear understanding of the functions and the principles of the helmet.

S1: initializing a balanced state parameter for safe usage after the user of the vehicle wears the helmet;

S2: acquiring a running speed Vz of the vehicle along the Y-axis;

S3: acquiring a head rotation angle $\theta x$ of the user along the X-axis and a head rotation angle $\theta y$ of the user along the Y-axis;

S4: detecting a duration time T of an action with a rotation angle exceeding a safe rotation angle;

S5: processing data of Vz, $\theta x$, $\theta y$ and T to determine whether to output an alarm; and S6: outputting an alarm or returning to the step S2.

In the illustrative working process, an alarm threshold must be preset in order to determine whether to output an alarm. In one example, the alarm threshold may be configured by various ways described as below.

An alarm condition may be configured as: a rotation angle of the user of the vehicle in the X-axis direction exceeds a threshold value $\theta x'$, and a duration time Tx during which the rotation angle exceeds the threshold value $\theta x'$ exceeds a time threshold; a rotation angle of the user of the vehicle in the Y-axis direction exceeds a threshold value $\theta y'$, and a duration time Ty during which the rotation angle exceeds the threshold value $\theta y'$ exceeds a time threshold; and a running velocity of the vehicle is larger than Vz'.

Initial data required to be acquired includes: a running velocity Vz of the vehicle in the Z-axis direction; a head rotation angular velocity $\omega x$ of the user of the vehicle in the X-axis direction and a time tx cost by the head rotation; and a head rotation angular velocity $\omega y$ of the user of the vehicle in the Y-axis direction and a time ty cost by the head rotation.

Data required to be calculated: a head rotation angle $\theta x(t)$ and a head rotation angle $\theta y(t)$ of the user of the vehicle at the time t; and a duration time Tx and a duration time Ty during which the head rotation angle exceeds the threshold value; wherein $\theta x(t)=\int \omega x dt$ and $\theta y(t)=\int \omega y dt$; calculating the duration time Tx by using a time when $\theta x(t)$ is greater than $\theta x'$ as a starting time; and calculating the duration time Ty by using a time when $\theta y(t)$ is greater than $\theta y'$ as a starting time.

Figure 5:
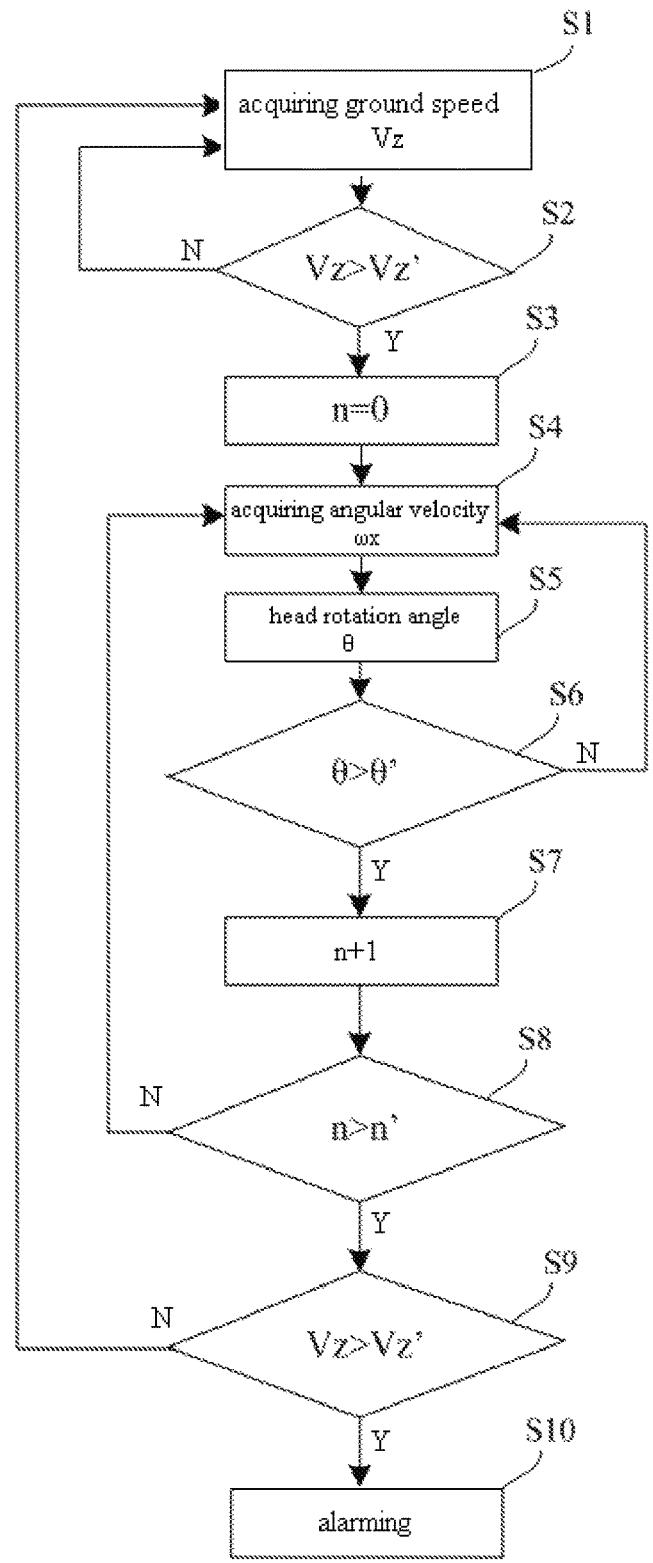
FIG. 5 is a flow chart of a control method of an illustrative head lowering and turning reminding device provided by an embodiment of the present disclosure.

More detailed description will be given below to the working flow of outputting an alarm for head lowering and turning with reference to FIG. 5.

The riding helmet with safety alarm function provided by the embodiment of the present disclosure may output an alarm in the case of safety risk caused by a head lowering or turning action of the user of the vehicle such as an electric bicycle last for a long time, so as to avoid traffic accidents.

It should be noted that: apart from the helmet, the head lowering and turning reminding device provided by the embodiment may also be manufactured in any other forms, for instance, a vehicle equipment. No specific limitation will be given in the embodiment.

Figure 4:
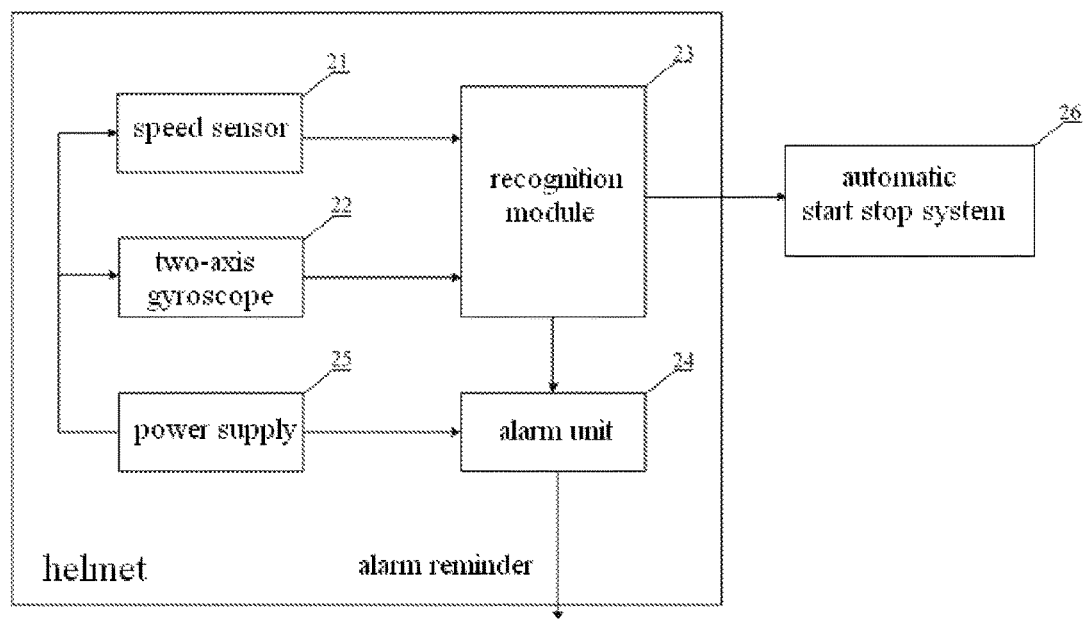
FIG. 4 is a schematic structural view of another illustrative head lowering and turning reminding device provided by the embodiment of the present disclosure.

In some examples, as illustrated in FIG. 4, an automatic start stop system 26 may also be disposed on a vehicle such as an automobile and a motorcycle. The automatic start stop system may control a speed of the vehicle, including controlling the vehicle to accelerate, to decelerate or to brake. In this case, the recognition module 23 in the riding helmet provided by the embodiment may also send a speed control signal to the automatic start stop system 26; at the same time when the alarm unit 24 outputs an alarm, the automatic start stop system 26 decelerates the vehicle according to the speed control signal, until the vehicle stops; the original speed of the vehicle may be gradually restored when the user no longer keeps the head lowering or turning action for long time; in this way, the safety risk caused by an absent-minded user can be avoided.

The embodiment of the present disclosure further provides a control method of the head lowering and turning reminding device. As illustrated in FIG. 5, the control method may include steps as below.

S1: acquiring a ground speed Vz of a vehicle;

S2: determining whether the ground speed Vz as acquired is greater than a preset speed threshold Vz';

S3: if the ground speed Vz is greater than the speed threshold Vz', assigning a value 0 to an action continuation parameter n (that is, n=0) and executing the step S4; or else, executing the step S1;

S4: acquiring an angular velocity ($\omega x$ or $\omega y$, and hereinafter the method is described with reference to $\omega x$ by way of example) of a head rotation action of a user of the vehicle and a time t cost by the head rotation action;

S5: calculating an angle $\theta$ of the head rotation action according to the angular velocity $\omega x$ and the time t cost by the head rotation action as acquired;

S6: determining whether the angle $\theta$ of the head rotation action is greater than a preset angle threshold $\theta'$, namely whether $\theta > \theta'$ is satisfied; if so, executing the step S7; if not, executing the step S4;

S7: adding 1 to the value of the action continuation parameter n;

S8: determining whether the current action continuation parameter is greater than a preset continuation threshold, namely whether n>n' is satisfied; if so, it's indicated that a duration time of the user' head holding a head lowering or turning action exceeds a preset value, then executing the step S9; it not, executing the step S4;

S9: acquiring the ground speed Vz of the vehicle again and determining whether the ground speed Vz is greater than the preset speed threshold Vz'; if so, executing the step S10; if not, executing the step S1; and S10: outputting an alarm for reminding the user.

The above steps S1 to S10 are described with reference to the case where the head rotation of the user is in the X-axis direction by way of example, namely a left-and-right rotation of the head. Actually, a head rotation action may also include head raising and lowering action in the Y-axis direction. At this point, the angular velocity in the control method, correspondingly, is the angular velocity wy of the rotation in the Y-axis direction. In addition, the preset continuation threshold n' is relevant to the duration time of the head rotation action. One of the possible settings is that: acquiring a time T0 required for executing the steps S3 to S7; and dividing a preset, permitted duration time of the action (which may be set based on experiments or experiences, and may also be adjusted by the user) by the required time T0 and rounding the division result to obtain the preset continuation threshold n'. For instance, if T0 is 0.5 s and the preset, permitted duration time is 30 s, the preset continuation threshold n' is 6.

In some examples, before the step S1, the control method further includes: initializing the speed sensor, the head posture monitoring module and the recognition module, so as to avoid the influence of the original data.

In some examples, in the step S4, the gyroscope is adopted to acquire the angular velocity of the head rotation action and the time cost by the head rotation action.

The control method provided by the embodiment of the present disclosure adopts the alarm module to output an alarm for reminding the user when the ground speed of the vehicle is greater than the speed threshold and the duration time of user holding the head lowering or turning action exceeds the preset time threshold; in this way, an alarm is activated in case of a head lowering or turning action last for a long time, so as to avoid traffic accidents.

It should be understood by those skilled in the art that all or partial of the working flows for implementing the control method may be completed by computer program instructions in combination with relevant hardware. The program instructions may be stored in a computer-readable storage medium. The program instructions may execute the working flows of the methods when executed on, for instance, a processor. The storage medium may be a disk, a compact disc (CD), a read-only memory (ROM), a random-access memory (RAM), etc.

Obviously, various modifications and deformations can be made to the present disclosure by those skilled in the art without departing from the spirit and scope of the present disclosure. Therefore, the present disclosure is intended to include the modifications and deformations fallen within the scope of the appended claims and equivalents thereof.

The present application claims the benefits of Chinese patent application No. 201610105874.2, filed Feb. 25, 2016, titled "Head Lowering and Turning Reminding Device, Control Method thereof and Helmet" which is incorporated herein by reference as part of the application.

The invention claimed is:

1. A head lowering and turning reminding method for a driver of a vehicle, comprising:
    S1: acquiring, via a speed sensor, a ground speed of the vehicle, the ground speed being a running velocity $V_z$ of the vehicle in a Z-axis direction;
    S2: determining, through a first determination sub-module of an alarm module, whether the running velocity $V_z$ as acquired is greater than a preset speed threshold $V_z'$;
    S3: if the running velocity $V_z$ is greater than the preset speed threshold $V_z'$, assigning a value 0 to an action continuation parameter n, through a second determination sub-module of the alarm module, and executing the step S4; or else, executing the step S1;
    S4: acquiring, through a head posture monitoring module, a head rotation angular velocity $\omega_x$ of the driver in a X-axis direction, a time $t_x$ cost by the head rotation, a head rotation angular velocity $\omega_y$ of the driver in a Y-axis direction, and a time $t_y$ cost by the head rotation;
    S5: calculating, through the head posture monitoring module, a head rotation angle $\theta_x(t)$ and a head rotation angle $\theta_y(t)$ of the driver at time t according to $\theta_x(t)=\int \omega_x d_t$, $\theta_y(t)=\int \omega_y d_t$;
    S6: determining, through a recognition module, whether the head rotation angle $\theta_x(t)$ and the head rotation angle $\theta_y(t)$ of the driver at the time t are greater than a preset angle threshold $\theta x'$ and a preset angle threshold $\theta y'$, respectively; if so, executing the step S7; and if not, executing the step S4;
    S7: adding 1 to the value of the action continuation parameter n, through the second determination sub-module of the alarm module;
    S8: determining whether the action continuation parameter n is greater than a preset continuation threshold n', through the second determination sub-module of the alarm module; if so, executing the step S9; and if not, executing the step S4;

S9: acquiring, via the speed sensor, the running velocity $V_z$ of the vehicle in the Z-axis direction again, and determining whether the running velocity $V_z$ is greater than the preset speed threshold $V_z'$, again through the first determination sub-module of the alarm module; if so, executing the step S10; and if not, executing the step S1; and S10: outputting, through a prompt sub-module of the alarm module, an alarm for reminding the driver;

S11: sending a first speed control signal to the vehicle, through the recognition module, at the same time when outputting the alarm, through the prompt sub-module of the alarm module, to decelerate the running velocity $V_z$ of the vehicle in the Z-axis direction until the vehicle stops; and S12: sending a second speed control signal to the vehicle, through the recognition module, to restore an original running velocity $V_z$ of the vehicle in the Z-axis direction if no head lowering or turning action for a duration time exceeding a preset time threshold is detected through S4-S8 after the vehicle stops.

2. The head lowering and turning reminding method according to claim 1, wherein the head rotating action comprises: a head raising action toviz wherein the head moves upwards, a head lowering action wherein the head moves downwards, and a head turning action wherein the head moves leftwards and rightwards.

3. The head lowering and turning reminding method according to claim 1, wherein the preset continuation threshold n' is configured by:
acquiring a time T0 required for executing the steps S3 to S7; and
dividing a preset action duration time by the time T0, and rounding the division result to obtain the preset continuation threshold n'.

4. The head lowering and turning reminding method according to claim 1, further comprising:
before the step S1, initializing the speed sensor, the head posture monitoring module, and the recognition module.

5. The head lowering and turning reminding method according to claim 1, wherein, in the step S4, a gyroscope is adopted to acquire the head rotation angular velocity and the time cost by the head rotation.

6. A head lowering and turning reminding device disposed on a vehicle or worn by a driver of the vehicle, for performing the head lowering and turning reminding method according to claim 1, comprising:
the speed sensor configured to detect the ground speed of the vehicle;
the head posture monitoring module configured to monitor a head posture of the driver and generate a signal relevant to a head rotating action of the driver;
the recognition module configured to receive the signal generated by the head posture monitoring module, and recognize at least one action of a head lowering action and a head turning action of the driver and a duration time of the driver holding this action according to the signal; and
the alarm module configured to output the alarm for reminding the driver upon the ground speed of the vehicle being greater than a speed threshold and the duration time of the driver holding the head lowering action or the head turning action exceeding the preset time threshold, wherein
the recognition module is further configured to send the first speed control signal to the vehicle at the same time when the alarm module outputs the alarm to decelerate the vehicle according to the first speed control signal until the vehicle stops, and, to send the second speed control signal to the vehicle to restore the ground speed of the vehicle if no head lowering or turning action for a duration time exceeding the preset time threshold is detected after the vehicle stops.

7. The head lowering and turning reminding device according to claim 6, wherein the head posture monitoring module is a gyroscope.

8. The head lowering and turning reminding device according to claim 6, wherein the head posture monitoring module comprises a compass.

9. The head lowering and turning reminding device according to claim 6, wherein the speed sensor is a laser velometer or a radar velometer.

10. The head lowering and turning reminding device according to claim 6, wherein the recognition module is a microcontroller.

11. The head lowering and turning reminding device according to claim 6, further comprising:
a power module configured to supply power for the speed sensor, the head posture monitoring module, the recognition module, and the alarm module.

12. A helmet, comprising the head lowering and turning reminding device according to claim 6.

13. The helmet according to claim 12, wherein the head posture monitoring module is a gyroscope.

14. The helmet according to claim 12, wherein the head posture monitoring module comprises a compass.

15. The helmet according to claim 12, wherein the speed sensor is a laser velometer or a radar velometer.

16. The helmet according to claim 12, wherein the recognition module is a microcontroller.

17. The helmet according to claim 12, wherein the head lowering and turning reminding device further comprises:
a power module configured to supply power for the speed sensor, the head posture monitoring module, the recognition module, and the alarm module.

* * * * *